United States Patent [19]

Desai et al.

[11] Patent Number: 4,784,845
[45] Date of Patent: Nov. 15, 1988

[54] EMULSION COMPOSTIONS FOR THE PARENTERAL ADMINISTRATION OF SPARINGLY WATER SOLUBLE IONIZABLE HYDROPHOBIC DRUGS

[75] Inventors: Narendra R. Desai, Danbury, Conn.; Edward C. Shinal, Old Tappan, N.J.; Madurai Ganesan, Pomona; Eugene A. Carpentier, Spring Valley, both of N.Y.

[73] Assignee: American Cyanamid Company, Stamford, Conn.

[21] Appl. No.: 776,306

[22] Filed: Sep. 16, 1985

[51] Int. Cl.$^4$ .................... A61K 31/02; A61K 31/08; A61K 31/16; A61K 31/40

[52] U.S. Cl. ...................... 424/80; 424/439; 514/938; 514/943; 514/939

[58] Field of Search .................... 424/80, 38; 514/938, 514/939, 943

[56] References Cited

U.S. PATENT DOCUMENTS

| | | | |
|---|---|---|---|
| 3,172,816 | 3/1965 | Swintosky | 514/943 |
| 3,647,624 | 3/1972 | Evenson | 435/2 |
| 3,991,206 | 11/1976 | Tolman et al. | 424/317 |
| 3,996,934 | 12/1976 | Zaffaroni | 128/268 |
| 4,124,720 | 11/1978 | Weinmaekers | 514/943 |
| 4,125,603 | 11/1978 | Audibert et al. | 514/938 |
| 4,168,308 | 9/1979 | Wretlind et al. | 514/938 |
| 4,340,054 | 7/1982 | Michaels | 128/260 |
| 4,563,354 | 1/1986 | Chang et al. | 514/938 |
| 4,610,868 | 9/1986 | Fountain et al. | 424/1.1 |
| 4,647,586 | 3/1987 | Mizushima et al. | 514/532 |
| 4,670,255 | 6/1987 | Yoshizumi et al. | 424/93 |
| 4,703,062 | 10/1987 | Blackburn et al. | 514/552 |

FOREIGN PATENT DOCUMENTS

| | | |
|---|---|---|
| 1127039 | 7/1982 | Canada . |
| 58-59912 | 4/1983 | Japan . |
| 2105589 | 3/1983 | United Kingdom . |

*Primary Examiner*—Ronald W. Griffin
*Attorney, Agent, or Firm*—R. P. Raymond

[57] ABSTRACT

This disclosure describes quick breaking, in vivo, intravenous, intramuscular, intraarticular fat emulsion compositions which incorporate the use of benzyl alcohol as a consurfactant and/or a cosolvent in combination with materials such as synthetic surfactants, e.g. sorbitan triisostearate, triglycerol diisostearate or triglycerol pentaoleate; naturally occurring vegetable oils, e.g. sesame oil, and soybean oil; natural lecithins such as egg lecithin or soy lecithin; saturated or unsaturated aliphatic acids, e.g. oleic acid, hexanoic acid and linolenic acid; and other excipients such as glycerine, polyvinylpyrrolidone, Pluronic® F-68 and di-α-tocopherol.

27 Claims, 2 Drawing Sheets

EMULSION COMPOSTIONS FOR THE PARENTERAL ADMINISTRATION OF SPARINGLY WATER SOLUBLE IONIZABLE HYDROPHOBIC DRUGS

BACKGROUND OF THE INVENTION

Emulsion systems have been used as dosage forms, normally for the oral administration of oils, or in the form of topical products or cosmetics. At the present time, emulsions also have utility as parenteral drug delivery systems. L. D. Pelham, Am. J. Hosp. Pharm., 38: 198-208 (1981), reports total parenteral nutrition (TPN) has been one of the most important advances in acute patient care over the past decade. It is a means of providing intravenous nutrition to patients who are unable to absorb nutrients via the gastrointestinal tract. Infused nutrients may include amino acids, dextrose, electrolytes, minerals, vitamins, fatty acids and trace minerals.

As reported by L. D. Pelham in the prior cited reference, intravenous fat emulsions have been commercially available in European countries for over 20 years though their use in the United States has been restricted until recently because of severe and infrequently fatal reactions as reported in the Br. J. Surg., 52: 795-800 (1965) and Drug Intell. Clin. Pharm., 6: 321-30 (1972). Lipomul®, the first intravenous fat emulsion introduced in the United States, was withdrawn in 1965 following several reports of a "fat overloading syndrome" as described in the Br. J. Surg., 52: 291-8 (1965) and Metabolism 6: 815-21 (1957). Intralipid®, distributed by Cutter Laboratories was approved for use in the United States in 1975, it had previously been used in Europe for years. In 1979, Liposyn®, a second intravenous fat emulsion, was marketed by Abbott Laboratories.

Intralipid® and Liposyn® contain 10% w/v or 20% w/v soybean oil and 10% w/v safflower oil respectively, as a source of polyunsaturated fatty acids. Each product contains 1.2% w/v of purified egg phospholipids as an emulsifier and water is added to make a 10% w/v or 20% w/v emulsion. Until recently over 10% emulsions were available in the U.S. In Europe 20% emulsions constitute the majority of use as reported in Surg. Clin. North Am., 58: 1055-70 (1978). Glycerol, a water-soluble substance, is added to make fat emulsions isotonic, with 2.25% w/v in Intralipid® and 2.5% w/v in Liposyn®. Since fat exerts a minimal osmotic pressure, glycerol contributes twice the osmotic load as an equal weight of glucose, mannitol, or sorbitol according to the N. Engl. J. Med., 297: 1444-52 (1977). Both Intralipid® and Liposyn® have a pH range of 5.5 to 8 and emulsified fat particles in Intralipid® and Liposyn® range from 0.1 to 0.5 $\mu$m in diameter, slightly smaller than endogenous chylomicrons as reported in several references, including Metabolism, 27: 1109-27 (1978).

Since the early 1970's most reports in the literature for adverse reactions attributed to fat emulsions related to the use of Intralipid® simply because it was the only commercially available fat emulsion. Similar adverse reactions may be reported for Liposyn® with the passage of time. Intralipid® and Liposyn® appear to have significantly fewer and milder adverse reactions than Lipomul® as reported in Can. Med. Assoc. J., 111: 152-4 (1974) and Liposyn® Research Conference proceedings. North Chicago; Abbott Laboratories (1979). Most serious reports today are associated with excessive doses as reported in Arch. Surg., 111: 1391-3 (1976).

Two types of adverse reactions occur with fat infusions. The first type is usually acute or mild and occurs during the infusion. The second type occurs later with prolonged use of intravenous fat emulsions. The most commonly reported acute reactions include a febrile response, chills and shivering and pain in the chest or back, described in J. Pediatr., 86: 2-16 (1975). Very rapid infusions may cause palpitations, tachypnea, sudden tightness of the chest, wheezing, cyanosis, nausea, pain at injection site, oily taste and headache as reported in Br. J. Surg., 52: 291-8 (1965). During recent years the intravenous fat emulsions which are initially reserved for the provision of essential fatty acids have gained in popularity as a caloric source as described in U.S. Pat. No. 3,169,094 and by M. T. Yeo, et al. in Arch. Surg., 106: 792-6 (1973). As reported by R. Jeppsson and S. Ljungberg in Acta Pharmacal. et. Toxical, 36: 312-20 (1975). Ljungberg and Jeppsson investigation pharmacodynamic effects of using emulsions as vehicles for lipid soluble materials in 1970, '72 and '73. Effects were investigated after parenteral administration of soybean oil emulsions containing various drugs dissolved in the oil phase. The drugs studied were barbituric acids, cyclandelate nitroglycerin and diazepam. The results indicated that the emulsion formulations would be suitable vehicles for lipid soluble drugs intended for intravascular administration, since the pharmacological effects were nearly equal to those found after a water solution of the sodium salts. A prolongation of anesthesia was observed for barbituric acids when administered in the oil phase of a soybean emulsion as compared with a solution of the corresponding sodium salt. The results were explained as a slow release of the drug from the oil particles or, the possibility of a more specific delivery of the drugs to the central nervous system when the drug is contained in oil droplets [R. Jeppsson, Acta pharmaceutica sueccia, 9, 81-90 (1972)]. A commercial diazepam product has been reported as being available by O. Dardel, et al., Anaesth. Scand., 20: 221-24 (1976). This lipid emulsion formulation was prepared by Vitrum AB, Sweden and shows many similarities to Intralipid®. The new lipid emulsion form was found to significantly reduce the incidence of local side effects involving the venous system and no significant difference in the therapeutic effect of the different preparative forms of diazepam was observed.

SUMMARY OF THE INVENTION

The present invention relates to compositions of matter comprising quick breaking, in vivo, intravenous, intramuscular, intraarticular and/or oral fat emulsion form preparations which incorporate the use of benzyl alcohol as a cosurfactant and/or a cosolvent in combination with materials such as synthetic surfactants, e.g. sorbitan triisostearate, triglycerol diisostearate or triglycerol pentaoleate; naturally occurring vegetable oils, e.g., sesame oil and soybean oil; natural lecithins such as egg lecithin or soy lecithin; saturated or unsaturated aliphatic acids, e.g., oleic acid, hexanoic acid and linolenic acid. Other excipients may optionally be included, such as glycerine, polyvinylpyrrolidone, Pluronic® F-68 and dl-$\alpha$-tocopherol. Said preparations are designed to solubilize certain sparingly water soluble hydrophobic ionizable drugs and certain water insoluble hydrophobic viscous oily liquids and/or those basic drugs which have negative logarithms of ionization constants, i.e., pK's, lower or nearer the physiological pH or, in the case of acidic drugs, a negative logarithm of ionization constant or constants i.e., pK's higher or nearer the physiological pH.

Thus, in the case of acidic drugs (with lower or nearer negative logarithms of ionization constants, i.e., pK's than the physiological pH) or basic drugs (with higher or nearer negative logarithms of ionization constants, i.e., pK's), when introduced in a physiological environment (e.g. I.V. infusion) they are converted into molecular forms of considerably lowered solubilities. As a result, the drugs precipitate, resulting in localized high accumulation of potentially irritating compounds.

pK's are inherent molecular properties which cannot be changed without making covalent modifications in the structure of a compound. At a somewhat later stage in the history of the preclinical pharmaceutical development of the compound, if covalent changes in the structure are made the chemical is considered a new chemical entity and thus all the pharmaceutical, pharmacological, toxicological, pharmacokinetic and other biological data have to be repeated. Also, many times covalent structure modification results in loss or reduction or complete change in the pharmacological activity. This invention, describing quick-breaking (or quick drug releasing) emulsion drug delivery liquid system, circumvents the local precipitation of drugs without making covalent modification in the structure of the problem drugs.

Certain antitumor agents such as bis(2-imidazolen-2-ylhydrazone)-9,10-anthracenedicarboxaldehyde (disclosed in U.S. Pat. No. 4,258,181 and hereinafter referred to as bisantrene base) and adriamycin base disclosed in U.S. Pat. No. 3,590,028 or the like, are examples of hydrophobic drugs which may be solubilized by this procedure. The compound 3-[4,6-bis[(1,2-2,2-tetramethylpropyl)amino]-s-triazin-2-yl]-3-azabicyclo[3.2.2]nonane which has utility as an antiarthritic agent and is disclosed in U.S. Pat. No. 4,261,892 is also a sparingly water soluble hydrophobic ionizable drug and may be successfully formulated with a fat emulsion vehicle as well. This solubilized drug in the emulsified preparation may also be administered by the intravenous route without harmful side effects.

It is contemplated that the emulsion solubilization systems described herein may have application with a number of other drug substances, some of which are known commercial products and others which are reported in the literature, e.g.; Triamterene, a diuretic found in U.S. Pat. No. 3,081,230 (1963 to Smith, Kline & French); Amphotericin B, an antifungal agent: Gold, et al., Antibiot. Ann. 1955-1956, 579; or U.S. Pat. No. 2,908,611 (1959 to Olin Mathieson); Ibuprofen, an anti-inflammatory agent, in U.S. Pat. No. 3,385,886 (1968 to Boots Pure Drug Company Ltd.); Indomethacin, an anti-inflammatory agent, in U.S. Pat. No. 3,161,654 (1964 to Merck & Co.); Terfenadine RMI-9918, an antihistamine without CNS effects is disclosed in Annual Drug Data Report, 3: 246 (1981) (Richardson-Merrell Inc.); (triphenylphosphoranylidene)carbamic acid, ethyl ester, has an undisclosed pharmaceutical activity, and is disclosed in East German Pat. No. 137,716; the compounds phenyl[7-(4-pyridinyl)pyrazolo[1,5-a]pyrimidin-3-yl]methanone and 2-furanyl[7-(3-pyridinyl)pyrazolo[1,5-a]pyrimidin-3-yl]methanone, which have utility as anxiolytic agents, are disclosed in patent application, Ser. No. 506,966, filed June 23, 1983 by the American Cyanamid Co.; the compound 5-(3-bromophenyl[1,2,4]triazolo[1,5-c]pyrimidin-2-amine, an antiasthmatic agent, in patent application, Ser. No. 518,250, filed July 28, 1983 by the American Cyanamid Co.; and Cisplatin hydrophobic complexes such as 2-hydrazino-4,5-dihydro-1H-imidazole compound with platinum chloride ($PtCL_2$) (1:1) and 5-hydrazino-3,4-dihydro-2H-pyrrole, compound with platinum chloride, both of which are active as antineoplastic agents and are disclosed in patent application, Ser. No. 553,675, filed on Nov. 21, 1983 by the American Cyanamid Co.

Examples of other commercial acidic drugs, which precipitate in varying amounts at the physiological pH upon the intravenous infusion, are the following.

TABLE IA

| Trade Mark | Ambient Solution pH | pH beyond which significant precipitation occurs |
|---|---|---|
| Droperidol (dehydrobenzperidol) | 3.24 | 5.83 |
| Thalamonal | 3.44 | 6.00 |
| Dipidolor (piritramide) | 3.97 | 4.50 |
| Phenergan (promethazine) | 5.68 | 6.42 |
| Largactil (chloropromazine) | 5.75 | 6.50 |
| Nozinan (levomepromize) | 4.38 | 6.50 |
| Prazine (promazine) | 4.85 | 7.10 |
| Atarax (hydroxyzine) | 5.60 | 6.40 |
| Inderal (propanolol) | 3.50 | 6.00 |
| Aramine (metaraminol) | 3.60 | 5.80 |
| Persantine (dipyridamole) | 3.12 | 5.10 |
| Eraldin (practolol) | 5.80 | 7.40 |

DETAILED DESCRIPTION OF THE INVENTION

Figure 1:
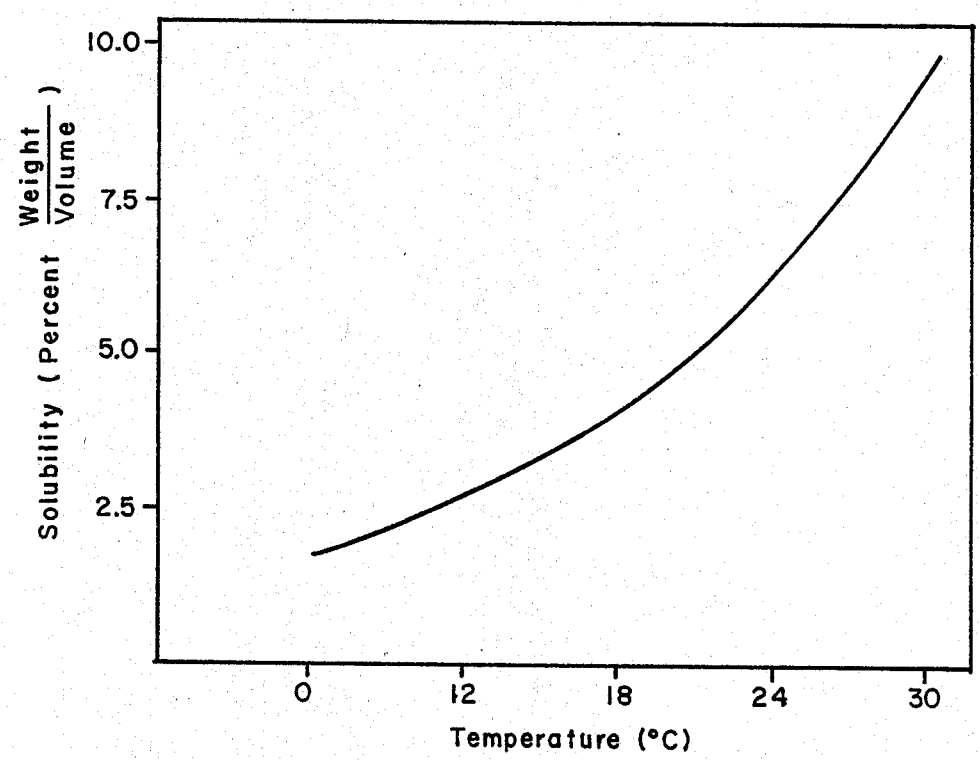
FIG. 1 is a graph of the solubility of a hydrophilic drug.

As previously disclosed hereinabove, benzyl alcohol has been successfully utilized as a cosolvent and/or cosurfactant in the present invention to aid in the solubilization of certain sparingly water soluble hydrophobic ionizable drugs.

Benzyl alcohol is a common preservative in the diluent of intravenous drugs at a concentration of 0.9% (w/v) and may be found in varying somewhat higher amounts in other commercial products, e.g., E. R. Squibb & Sons Inc., Princeton, N.J. markets Prolixin Decanoate ® a behavior modifier which is available for intramuscular or subcutaneous administration, providing 25 mg of fluphenazine decanoate per ml in a sesame oil vehicle with 1.2% (w/v) benzyl alcohol as a preservative. Squibb also markets Vesprin ® Injection, a tranquilizing agent available for parenteral use in multiple dose vials providing 10 or 20 mg of trifluoropromazine hydrochloride per ml with 1.5% benzyl alcohol as a preservative, etc. Organon Pharmaceuticals, West Orange, N.J. markets Deca Durabolin ® an anabolic agent (nandrolone decanoate injection U.S.P.) dissolved in sterile sesame oil solution for intramuscular injection, available in a potency of 50 mg/ml with 10% benzyl alcohol preservative; 100 mg/ml with 10% benzyl alcohol and 200 mg/ml with 5% benzyl alcohol preservative. Organon also markets Durabolin ® (nandrolone phenpropionate injection U.S.P.) in sterile sesame oil solution for intramuscular injection, available in potencies of 25 mg/ml with 5% benzyl alcohol preservative and 50 mg/ml with 10% benzyl alcohol preservative.

The use of materials such as propylene glycol, benzyl alcohol and ethyl alcohol as solvents for intravenous preparations of Diazepam has been discussed in Acta anaesth. scand. 20, 221–224 (1976). It was reported that these solutions may not only cause pain upon intravenous injection, but also thrombophlebitis.

An article entitled "The Tolerance and Safety of Intravenously Administered Benzyl Alcohol in Methylprednisolone Sodium Succinate Formulations in Normal Human Subjects", found in Toxicol. Appl. Pharmacol. 23, 54–61 (1972) reports that two methylprednisolone sodium succinate formulations with different preservatives (benzyl alcohol and parabens) and a placebo were administered in single doses of 2.0 g to 24 subjects. The formulations were well tolerated and no important drug-related side effects were encountered. No clinically significant changes in vital signs, electrocardiograms, electroencephalograms, or laboratory parameters were noted. All expected corticosteroid induced changes were reversible. The higher antibacterial activity of benzyl alcohol shown in the challenge tests plus comparable tolerance to parabens favored the use of benzyl alcohol as a preservative. A discussion concerning the toxicity of intravenous benzyl alcohol found in Drug Intelligence Clin. Pharm. 9(3): 154–155 (1975) reports salient evidence to the absence of acute systemic toxicity from 0.9% (w/v) benzyl alcohol. The posed possibility of chronic toxicity in patients receiving long term intravenous therapy which requires repeated administration of drug and diluents was discussed in Toxicol. Appl. Pharmacol. 18, 60 (1971). Benzyl alcohol has a short half-life of 1.5 hours and a volume of distribution which indicates widespread tissue dissemination. Since benzyl alcohol is metabolized via a first order oxidative scheme to benzoic acid which is catabolized in sequence by another first order process via conjugation with glycine to hippuric acid or secondarily with glucuronide, tissue accumulation should not be a contributory problem with these rapid processes.

The present invention encompasses the compositions of matter hereinafter to be described and the method of treatment therewith.

In many instances in the treatment of humans or animals with drugs it may be necessary to administer the drug by the intravenous route. Intravenous administration is the quickest and most direct means of drug delivery. However, local intravenous injection site adverse reactions may occur which could be due to: (a) thermodynamically driven local precipitation of a potentially irritating drug in high amounts; (b) inherent quality of the drug to preferentially bind with the injection site tissue and hence cause high local accumulation of the drug; and (c) needle damaged vein leading to extravasation and then attack by the drug of the exposed tissue.

As reported in Acta Anesthesiologica Belgica, No. 3, 230–240 (October) 1973; even without obvious bacterial contamination, local thrombophlebitis is very common with intravenous infusions or injections. With infusions this problem occurred in approximately 30 percent of the cases studied no matter whether a needle, a metal or plastic cannula was used. Other series showed an incidence of post-infusion thrombophlebitis of 25–30 percent, whereas in 32 percent of the cases the complication symptoms did not appear until after one week. Also findings reported in Drug Intelligence and Clinical Pharmacy, 3, 266 (May) 1977 showed that 33 percent of all IV administered anticancer drugs were associated with the development of thrombophlebitis. Suggested solutions to the problem were directed to (a) consideration of needle or catheter size versus blood vessel diameter, (b) consideration of the density of infused solutions and (c) a new split type needle or catheter.

As previously mentioned, the intravenous route offers a direct and rapid means of drug administration and as reported in a recent article on Extravasation in Drug Intelligence and Clinical Pharmacy, 17, 713 (October) 1983 it is not a simple method, but one that requires special equipment, skilled personnel and close monitoring. One of the hazards of this route is the accidental misdirection of IV fluid and medication from a vein into the interstitial tissue. This could occur by slippage of an IV cannula from a vein into the tissue or when the IV fluid leaks from the vein through a puncture in the vein or around the cannula site. This article reports that extravasation was found to occur in 11 percent of IV treatments administered to children in cases studied and in as many as 22.8 percent of IV treatments in adults studied. Fortunately, most of these mishaps are recognized quickly and little harm results. Although it was determined that a small percentage of cases resulted in tissue damage due to extravasation, damage resulting from extravasation can be severe and can lead to a longer hospital confinement than originally intended. The initial presentation of an extravasation injury depends on the character of the medication and the volume of solution that has entered the interstitial tissue. In its simplest form, extravasation injury can appear as a painful, erythematous swelling surrounding the IV cannula site. If only part of the skin thickness is damaged, the area may appear blistered, with mottling and darkening of the skin. When the full thickness of the skin is damaged, the surface may appear very white and later may develop as a mass of dead tissue.

A review of the problems associated with the prevention and treatment of local toxicities caused by extravasation of cancer chemotherapeutic drugs may be found in Cancer Treatment Reviews, 7: 17–27 (1980). As described in Seminars in Oncology, 9 No. 1, 14–22 (March) 1982; most of the veins used for administration of chemotherapy course between the dermis and subcutaneous fat. Extravasation of toxic drugs can cause a full thickness loss of skin above the affected area. In areas of little subcutaneous fat such as the upper surface of the hand and around joints, severe damage to nerves, tendons and muscle can also occur. Some remedies suggested to reduce the chance of extravasation were (a) to use a freely flowing IV line, injecting normal saline before and after a venipuncture injection, (b) avoiding the antecubital fossa and hand, (c) using the proper flow rate and (d) using only the venous side of an arteriovenous fistula. However, it is reported that many cancer patients have such poor veins that occasional extravasation cannot be avoided.

Adverse injection site reactions described below for Adriamycin (Doxorubicin) are common for many drugs, with physiologically inconvenient ionization characteristics leading to precipitation at and/or binding of drugs with local tissues, when given by the parenteral route. On top of this when there is an accidental extravasation the problems become very severe.

A problem encountered with the intravenous administration of Adriamycin in cancer therapy is reported in Plastic and Reconstructive Surgery, 61: 86–92 (1978).

When the drug extravasates into the soft tissues it causes massive tissue necrosis about the site of the attempted intravenous administration. This necrosis develops at a slow rate, continues to increase in severity for several weeks, and does not heal in the usual manner. The resulting ulcers are indolent, and may remain a source of severe pain and functional impairment for many months without healing. Removal of the necrotic area and surrounding tissues containing the extravasated drug is recommended. Skin grafts take poorly if there are small amounts of the drug left in the tissue of the recipient site.

When an aqueous solution of bisantrene dihydrochloride is injected intravenously in mammals a problem which is likely to occur is chemical phlebitis [Cancer Research, 43: 925-29, (February 1983)]. On the basis of available information, it appears that the phlebitis is caused due to precipitation of the drug from the I.V. solution when mixed with venous blood. The occurrence of particles of drug on the surface of the vein results in local high concentrations for extended periods of time and produces irritation.

Figure 2:
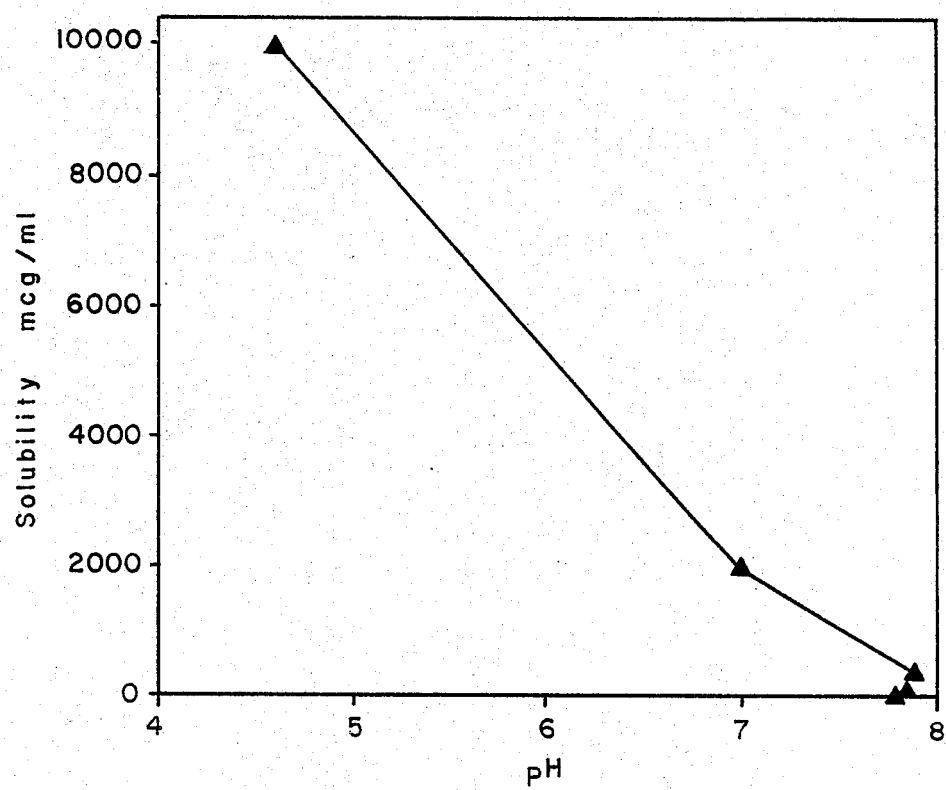
FIG. 2 is a graph of the solubility of a hydrophobic drug.

The solubility characteristics of the drug, which in turn affect precipitation, are very sensitive to temperature changes, pH, and various solutes. For example, FIG. 1 indicates the sensitivity of bisantrene solubility in water at pH 4.5 over a temperature range of 6° C. to 30° C., while Table IB indicates the wide range of its solubility in selected media and biological fluids whose values are plotted in FIG. 2.

TABLE IB

| Solubility of Bisantrene in Selected Media | | |
|---|---|---|
| Medium | pH | Solubility(mcg/ml) |
| 5% Dextrose Solution | 4.6 | 10,000 |
| Normal Saline | 5.5 | 2,000 |
| Whole Blood | 7.9 | 400 |
| Plasma | 7.7-8.2 | 90 |
| Serum | 7.8 | 27 |

It can be seen from the table that the drug is quite soluble in media useful as candidates for I.V. infusions such as normal saline and 5% dextrose. In serum and plasma, however, due to increase in the pH, the solubility drops considerably and this may be the reason that the drug precipitates at the point of infusion. It is also observed that solubility in whole blood is much greater than in plasma and serum. From the drug's solubility characteristics and other information, it appears that the drug eventually partitions into the erythrocytes which then serve as slow release carriers. Thus, if the drug can be kept in solution long enough to allow complete dilution in the entire blood volume, then the partitioning should take place without the intermediate precipitation.

With regard to the antiarthritic compound 3-[4,6-bis[(1,1-2,2-tetramethylpropyl)amino]-s-triazin-2-yl]-3-azabicyclo[3.2.2]nonane(triazine), accumulated data indicates that this compound has insignificant solubility in water and is therefore not recommended as a candidate for traditional oral dosage forms such as tablets. Solubilities were determined in parenterally acceptable solvents and are listed in Table II. Results indicate that the solubility is in the range of 0.5 to 1.5 mg/ml for parenteral solvents. Orally and parenterally acceptable solutions of surfactants and polymers such as Tween 40, 60 or 80, polyethylene glycol 300 or polyvinylpyrrolidone did not increase the solubility by more than 0.5 to 1.0 mg/ml.

TABLE II

| Solubility of Antiarthritic Triazine Compound in Parenterally Acceptable Solvents | |
|---|---|
| Solvent | mg/ml |
| Benzyl Benzoate | 1.3 |
| Propylene Glycol Isostearate | 1.5 |
| Benzyl Alcohol | 0.8 |
| Dimethyl Acetamide | 0.7 |
| Ethanol USP | <0.1 |
| Propylene Glycol | <0.1 |
| 1,3-Butylene Glycol | 0.3 |
| Triacetin | 0.1 |
| Cremophor ® EL | 0.2 |
| Emulphor ® EL-620P | <0.1 |
| Propylene Glycolisostearate | 0.3 |
| Brij ® 35 2% Solution | 0.05 |

Because the antiarthritic triazine compound is a base, organic acids as counter-ions were studied to improve drug solubility. The succinate and cinnamate salt was prepared which increased the solubility of the drug in ethanol. Additional drug complexes were prepared with various organic and inorganic acids. Some acids such as hippuric, suberic and phosphoric gave minor improvements in drug solubility in water. Preliminary findings of candidate dosage forms indicated: (a) parenteral absorption of the drug was negligible and (b) oral absorption was slightly better, however, about 90% of the compound was excreted in the feces. The inherent insolubility of the drug appears to be responsible, to some extent, for the preceding results. In order to overcome the drug insolubility problem one of the objectives considered was to design a dosage form which would improve drug absorption when given by intravenous, intramuscular or intra-articular injection.

An oil in water emulsion delivery system provides an advantageous solution to formulation and delivery problems, in that:
1. Local high concentration contact of the drug with blood component and tissue material could be minimized.
2. Containment of the drug in the oil phase of the oil in water emulsion with a controlled rapid release would allow the drug to travel away from the injection site without being precipitated.
3. The apparent limiting drug solubility in vivo (blood) could be increased in the proper emulsion formulation.
4. The localized immobilization of the drug at the injection site, because of its inherent property of precipitation at, or binding with the tissue reduces the bioavailability of potentially toxic drug. By having a biodegradable barrier effect of the emulsion, drug immobilization is eliminated, thus increased bioavailability would reduce the minimum effective dose and increase the therapeutic index.
5. A considerable reduction in the cardiac uptake of the drug may result.

The following emulsion associated characteristics are acknowledged to be essential factors to be considered when formulating the desired product:
1. All ingredients must be non-toxic and acceptable for parenteral administration;
2. All emulsion particles should be 5 microns or less (preferably in submicron range) in diameter otherwise they may obstruct the lung capillaries;

3. The emulsion should not aggregate on standing.
4. (a) The emulsion should be stable to the extent needed to carry the drug substantially away from the in vivo injection site, and thus reduce local site reactions.
    (b) However, the emulsion as a particle should not remain intact long enough to be selectively deposited in the liver and other reticuloendothelial system organs. Selective uptake in these organs is the fate of other particulate delivery systems such as microspheres, liposomes or routine emulsions.
5. The fat emulsion must withstand radiation sterilization and furthermore it is desirable that it endures wide temperature fluctuations near room temperature.
6. The fat emulsion shall withstand long time storage without breaking, creaming or flocculation.
7. A final demand is that the fat emulsions should be of a composition that should not have any adverse pharmacological influence on the blood pressure and the circulation and other physiological functions.

It has now been determined by us that by a suitable selection of a drug form, fats, emulsifiers, surfactants, cosurfactants, bacteriostats, preservatives, antioxidants and solvents, emulsion systems as carriers for lipid soluble drugs can be provided which can be supplied to mammals without side reactions.

The characteristic features of the novel emulsion system formulae of the present invention are derived from the various ingredients and combinations of ingredients therein, namely those which are encompassed by and included under the following categories: (1) an oleaginous vehicle or oil phase, (2) the active ingredient, (3) a surfactant or emulsifier, (4) a co-surfactant or auxilary emulsifier, (5) a cosolvent, (6) a bacteriostat or preservative, (7) a tonicity modifier or cryoprotectant, (8) an antioxidant, (9) an emulsion stabilizer and creaming preventor and (10) water.

The oil phase (1) may comprise of from about 5% to about 50% of the main formula, consisting essentially of (a) naturally occurring vegetable oils, e.g., well-refined or super refined sesame oil, peanut oil, olive oil, safflower oil, soybean oil and the like or an oleaginous vehicle such as benzyl benzoate; or (b) Semisynthetic mono, di or triglycerides utilized individually or in mixtures thereof, e.g., rac-glyceryl-1-monopalmitin, racglyceryl-1-monoolein, 1,2-dipalmitin, 1,3-dipalmitin, trimyristin, tripalmitin, tristearin, triolein, trielaidin, trilinolein, triheptadecanoic, and the like or fractionated or synthetic oils which may be exemplified respectively by Miglyol® 810 and 812, a mixture of caprylic and capric triglycerides manufactured from fractionated coconut oil by Dynamit Nobel Chemicals, Sweden, and Neobee® M5 a fractionated triglyceride of coconut oil origin that has been reconstituted to provide an alcohol soluble oil, manufactured by the Drew Chemical Corp., Boonton, N.J.

(2) The active ingredient may be a sparingly water soluble hydrophobic ionizable drug, a water insoluble hydrophobic viscous oily liquid and/or those which have ionization constants near the physiological pH.

The surfactants (3) may consist essentially of both water soluble and water insoluble types such as (a) natural lecithins or phospholipids derived from egg or soy sources and called egg or soy phosphatides, e.g., egg lecithin, egg phosphatidyl ethanolamine, phosphatidic acid, plant monogalactosyl diglyceride (hydrogenated) or plant digalactosyl diglyceride (hydrogenated) and the like; (b) synthetic lecithins such as dihexanoyl-L-α-lecithin, dioctanoyl-L-α-lecithin, didecanoyl-L-α-lecithin, didodecanoyl-L-α-lecithin, ditetradecanoyl-L-α-lecithin, dihexadecanoyl-L-α-lecithin, dioctadecanoyl-L-α-lecithin, dioleoyl-L-α-lecithin, dilinoleoyl-L-α-lecithin, α-palmito, β-oleoyl-L-α-lecithin, L-α-glycerophosphoryl choline and the like; (c) synthetic surfactants based on glycerine or sorbitol, e.g., sorbitan triisostearate, triglycerol diisostearate or triglycerol pentaoleate and the like, or those based on polyoxyethylated hydrocarbons or vegetable oils, e.g., Cremaphor® EL or RH40 and the like, Emulphor® EL-620P or EL-719 and the like or Arlacel® 186 and the like. Materials such as Pluronic® F-68, egg lecithin, soy lecithin and the like and certain $C_6$–$C_{20}$ saturated or unsaturated aliphatic acids may selectively be employed as a co-surfactant (4). Co-surfactants (4) may be selected from an alcohol such as isopropanol or benzyl alcohol and the like or may be selected from saturated or unsaturated aliphatic acids such as, caproic, enanthic, caprylic, capric, lauric, palmitic, stearic arachidonic, arachidic, oleic, linoleic, linolenic and the like. Another aspect of the present invention is concerned with the use of benzyl alcohol as a cosolvent (5) to aid in solubilizing the drug in the oil phase. The benzyl alcohol thus employed may also serve as a bacteriostat or preservative (6). A cryoprotectant or tonicity modifier (7) such as glycerol, lactose, mannitol and the like is optional and may be employed to provide protection against freezing and also serve as a means to establish and maintain a suitable osmotic pressure in the aqueous phase. The use of an antioxidant (8) is also optional and a material such as dl-α-tocopherol may be included in the formulation for this purpose. An emulsion stabilizer (9), e.g., Emulphor® EL-620P, Emulphor® EL-719 and the like may be used to prevent creaming of the drug emulsion. In all cases the completed drug form must be sterile and must be stable under the conditions of manufacture and storage and must be preserved against the contaminating action of microorganisms such as bacteria and fungi.

In the selection of the oleaginous vehicle or oil phase, surfactant, co-surfactant, emulsifiers and auxiliary emulsifiers, care should be taken to avoid selection of components which will interfere or chemically react with the hydrophobic drug. For example, certain preservatives, such as BHT and BHA are commonly contained in oil products, and such preservatives may react with hydrophobic drugs, such as bisantrene base. Accordingly, use of oils, or any other component of the emulsion formulation of the present invention having such additives or impurities should be avoided.

The invention will be described in greater detail in conjuction with the following specific examples.

EXAMPLE 1

Preparation of an Emulsion Drug Delivery System Containing 0.5 mg/ml Bisantrene Base

| Ingredient | Amount % W/V |
| --- | --- |
| Bisantrene Base | 0.05 |
| Sorbitan Triisostearate | 10.0 |
| Benzyl Alcohol | 2.0 |
| Sesame Oil(super refined) | 3.0 |
| Pluronic ® F-68 | 0.75 |

| Ingredient | Amount % W/V |
| --- | --- |
| Water for Injection | qs |

A 52.0 mg amount of bisantrene base (96.15%) was mixed and stirred at room temperature with 10.0 g of sorbitan triisostearate, 2.0 g of benzyl alcohol, 3.0 g of sesame oil and 750 mg of Pluronic® F-68 until complete solution was obtained. The volume of the mixture was adjusted to 100 ml with water for injection. The material was shaken well and sonicated for 20 seconds using a Branson Sonifier driver (Branson Instruments Inc., Stamford, CT) at a direct current setting of 6-7 amperes to provide an emulsion wherein 95% of the emulsion particles have a particle size from two to five microns.

EXAMPLE 2

Preparation of an Emulsion Drug Delivery System Containing 0.5 mg/ml Bisantrene Base

| Ingredient | Amount % W/V |
| --- | --- |
| Bisantrene Base | 0.05 |
| Triglycerol Diisostearate | 10.0 |
| Benzyl Alcohol | 3.0 |
| Sesame Oil(super refined) | 5.0 |
| Pluronic ® F-68 | 0.5 |
| Water for Injection | qs |

A 208.0 mg amount of bisantrene base (96.15%) was mixed and stirred at room temperature with 40.0 g of triglycerol diisostearate, 12.0 g of benzyl alcohol, 20.0 g of sesame oil and 2.0 g of Pluronic® F-68 until complete solution was obtained. The volume of the mixture was adjusted to 400 ml with water for injection. The mixture was shaken well and sonicated for 20 seconds and gave an emulsion wherein 93% of the particles were from two to five microns in size.

EXAMPLE 3

Preparation of an Emulsion Drug Delivery System Containing 0.5 mg/ml Bisantrene Base

| Ingredient | Amount % W/V |
| --- | --- |
| Bisantrene Base | 0.05 |
| Triglycerol Pentaoleate | 10.0 |
| Benzyl Alcohol | 2.0 |
| Sesame Oil(super refined) | 5.0 |
| Soy Lecithin 95% P.C. | 0.8 |
| Glycerine U.S.P. | 2.25 |
| Water for Injection | qs |

A 260 mg amount of bisantrene base (96.15%) was dissolved by stirring at room temperature in a mixture of 50.0 g of triglycerol pentaoleate, 10.0 g of benzyl alcohol, 25.0 g of sesame oil 4.0 g of soy lecithin and 11.25 g of glycerine. The total mixture was brought to a volume of 500 ml with water for injection and shaken well. The mixture was sonicated for 15 seconds in 80 ml portions. Then the entire batch was resonicated for a additional 30 seconds and gave an emulsion wherein 98% of the particles were at a range of 2-5 microns in size.

EXAMPLE 4

Preparation of an Emulsion Drug Delivery System Containing 1.0 mg/ml Bisantrene Base

| Ingredient | Amount % W/V |
| --- | --- |
| Bisantrene Base | 0.1 |
| Triglycerol Pentaoleate | 10.0 |
| Benzyl Alcohol | 2.0 |
| Sesame Oil(super refined) | 5.0 |
| Soy Lecithin 95% P.C. | 0.8 |
| Glycerine U.S.P. | 2.25 |
| Water for Injection | qs |

A 50.0 mg amount of bisantrene base (100%) was combined, mixed and stirred at room temperature with 5.0 g of triglycerol pentaoleate, 1.0 g of benzyl alcohol, 2.5 g of sesame oil, 400 mg of soy lecithin and 1.125 g of glycerine and gave a clear solution. Water for injection was added to adjust the volume to exactly 50.0 ml. The mixture was shaken, then sonicated as described in Example 1.

EXAMPLE 5

Preparation of an Emulsion Drug Delivery System Containing 1.0 mg/ml Bisantrene Base and With dl-α-Tocopherol as Antioxidant

| Ingredient | Amount % W/V |
| --- | --- |
| Bisantrene Base | 0.1 |
| Triglycerol Pentaoleate | 10.0 |
| Benzyl Alcohol | 2.0 |
| Sesame Oil(super refined) | 5.0 |
| Soy Lecithin 95% P.C. | 0.8 |
| dl-α-Tocopherol | 0.002 |
| Oleic Acid | 0.75 |
| Glycerin U.S.P. | 2.25 |
| Water for Injection | qs |

A 1.000 g amount of bisantrene base (100%) was combined, mixed and stirred at room temperature for 16 hours with 100.0 g of triglycerol pentaoleate, 20.0 g of benzyl alcohol, 50.0 g of sesame oil, 8.00 g of soy lecithin and 20.0 mg of dl-α-tocopherol in a ground glass stoppered erlenmeyer flask. The total weight of the mixture was 179.03 g. To a 170.07 g amount of this mixture was added, with swirling, 7.125 g of oleic acid and 21.375 g of glycerine in 300 ml of water for injection. The mixture was brought to a final volume of 950 ml with water for injection and mixed for 3 hours at room temperature. The mixture was homogenized at 8000 psi, four times in succession in a Gaulin homogenizer (Gaulin Corp., Everatt, MA) and gave a yellow emulsion.

EXAMPLE 6

Preparation of an Emulsion Drug Delivery System Containing 1.0 mg/ml Bisantrene Base and Formulated with Egg Lecithin

| Ingredient | Amount % W/V |
| --- | --- |
| Bisantrene Base | 0.1 |
| Triglycerol Pentaoleate | 10.0 |
| Benzyl Alcohol | 2.0 |
| Sesame Oil(super refined) | 5.0 |
| Egg Lecithin (60%) | 0.8 |
| dl-α-Tocopherol | 0.002 |
| Oleic Acid | 0.75 |

| Ingredient | Amount % W/V |
|---|---|
| Glycerin U.S.P. | 2.25 |
| Water for Injection | qs |

(1) A mixture of 8.00 g of egg lecithin (60%) in 50.00 g of sesame oil was mixed overnight at room temperature by magnetic stirring.

(2) A 1.000 g amount of bisantrene base was added to 20.00 g of benzyl alcohol in a 250 ml ground glass stoppered erlenmeyer flask. The mixture was mixed by magnetic stirring for about 20 minutes at room temperature and gave an orange suspension, then 100 g of triglycerol pentaoleate was added to this suspension and the material was mixed for 3 hours at room temperature.

(3) A 20 mg amount of dl-α-tocopherol in 60 mg of triglycerol pentaoleate was added to the preceding mixture, then the mixture from step 1 was added to the above and the total mixture was stirred magnetically for one hour. The mixture was warmed in a 56° C. oven for 45 minutes, then allowed to stand at room temperature for 16 hours. The total weight of this mixture was 179.080 g. To a 170.126 g amount of the above mixture was added with swirling 7.125 g of oleic acid and 21.375 g of glycerine in 300 ml of water for injection. The mixture was taken to a volume of 950 ml with water for injection and mixed for 19 hours at room temperature, then warmed at 40°–45° C. in a water bath for 15 minutes to complete solution. This material was homogenized as described in Example 5.

EXAMPLE 7

Preparation of an Emulsion Drug Delivery System Containing 2 mg/ml Bisantrene Base

| Ingredient | Amount % W/V |
|---|---|
| Bisantrene Base | 0.2 |
| Oleic Acid | 0.7 |
| Hexanoic Acid | 0.1 |
| Soybean Oil(super refined) | 5.0 or 7.0 |
| Soy Lecithin 95% P.C. | 1.2 |
| dl-α-Tocopherol | 0.01 |
| Benzyl Alcohol | 0.9 |
| Glycerin U.S.P. | 2.25 |
| Water for Injection | qs |

(1) A 2.46 g amount of bisantrene base, weighed from 93.86% "as is" material (including a 5% excess) and 7.7 g of oleic acid U.S.P. were dissolved in 48.34 g of chloroform with stirring at room temperature for about 40 minutes. The chloroform was removed in vacuo using a rotary evaporator. Then 9.900 g of benzyl alcohol and 1.100 g of hexanoic acid were added to the preceding mixture with stirring at room temperature.

(2) A 6.000 g amount of soy lecithin was dissolved in 35.000 g of soybean oil then 50.0 mg of dl-α-tocopherol was added and dissolved by stirring.

(3) An 11.25 g amount of glycerine U.S.P. was dissolved in about 100-150 ml of water for injection.

(4) The following materials were placed in a 42° C. walk-in incubator and allowed to equilibrate to that temperature: the oil phase mixture from step 1 containing bisantrene base, oleic acid, benzyl alcohol and hexanoic acid; the soy lecithin, soybean oil, tocopherol mixture of step 2; the glycerine and WFI solution of step 3; about 800 ml of WFI and two 500 ml Ⓢ graduated cylinders.

(5) A 4.809 g amount of the oil phase of step 1 was added to the entire mixture of step 2 and mixed by stirring. Then the glycerine/WFI solution of step 3 was added slowly with swirling. The combined mixture was transferred to a 500 ml Ⓢ graduated cylinder and brought to mark with WFI, stoppered and mixed thoroughly. The resulting emulsion containing 7.0% w/v soybean oil was passed through a Gaulin homogenizer four times in succession at a pressure of 8,000 psi.

An emulsion containing 5.0% w/v soybean oil was also prepared as described in steps 1, 2, 3, 4 and 5 above wherein a 25.000 g amount of soybean oil was substituted for the 35.000 g amount used in step 2 above.

EXAMPLE 8

Preparation of an Emulsion Drug Delivery System Containing 2 mg/ml Bisantrene Base

| Ingredient | Amount % W/V |
|---|---|
| Bisantrene Base | 0.2 |
| Oleic Acid | 0.4 |
| Hexanoic Acid | 0.1 |
| Linolenic Acid | 0.3 |
| Soybean Oil(super refined) | 7.0 |
| Soy Lecithin 95% P.C. | 1.0 |
| dl-α-Tocopherol | 0.01 |
| Benzyl Alcohol | 0.9 |
| Glycerin U.S.P. | 2.25 |
| Water for Injection qs ad | 100 |

The formulation above was prepared using the indicated percentages of ingredients and following the procedure of Example 7. The linolenic acid was added along with the hexanoic acid and benzyl alcohol as in step 1 of Example 7.

EXAMPLE 9

Preparation of an Emulsion Drug Delivery System Containing 2 mg/ml Bisantrene Base

| Ingredient | Amount % W/V |
|---|---|
| Bisantrene Base | 0.2 |
| Oleic Acid | 0.4 |
| Hexanoic Acid | 0.1 |
| Linolenic Acid | 0.3 |
| Soybean Oil(super refined) | 7.0 |
| Soy Lecithin 95% P.C. | 1.0 |
| dl-α-Tocopherol | 0.01 |
| Benzyl Alcohol | 0.9 |
| Polyvinylpyrrolidone Type N.P. K-90 | 0.04 |
| Glycerin U.S.P. | 2.25 |
| Water for Injection | qs |

The formulation above was admixed using the necessary quantities of ingredients and following the procedures of Examples 7 and 8. An aqueous solution of the polyvinylpyrrolidone type N.P. K-90 was prepared with WFI and added just prior to the addition of the glycerine/WFI in step 5 of Example 7.

EXAMPLE 10

Preparation of a Placebo for an Emulsion Drug Delivery System of Examples 3 and 4

| Ingredient | Amount % W/V |
|---|---|
| Triglycerol Pentaoleate | 10.0 |
| Benzyl Alcohol | 2.0 |
| Sesame Oil | 5.0 |
| Soy Lecithin 95% P.C. | 0.8 |
| Glycerine U.S.P. | 2.25 |
| Water for Injection | qs |

A 45.0 g amount of triglycerol pentaoleate was stirred and mixed at room temperature with 9.0 g of benzyl alcohol, 22.5 g of sesame oil, 3.6 g of soy lecithin and 10.125 g of glycerine and gave a clear viscous solution. Water for injection was added to adjust the volume to exactly 450 ml. The material was mixed, shaken and sonicated in 80 ml batches for 20 seconds each. The material was recombined and sonicated again for an additional 15 seconds and gave the desired product as a milky white emulsion.

The following Examples 11–15, of emulsion drug delivery systems were formulated and are proposed for the oral application of the antiarthritic drug 3-[4,6-bis[(1,1-2,2-tetramethylpropyl)amino]-s-triazin-2-yl]-3-azabicyclo[3.3.2]nonane. It is contemplated that the same emulsion systems can also be administered by the intravenous, intramuscular or intra-articular routes. However, since emulsions are efficient transporters of drugs, the total required dose for parenteral use may be much smaller. The systems described in Examples 11–15 are not necessarily final dosage forms.

EXAMPLE 11

Preparation of an Oral Emulsion Drug Delivery System Containing 0.5 mg/ml of Antiarthritic Drug

| Ingredient | Amount % W/V |
|---|---|
| 3-[4,6-Bis[(1,1-2,2-tetramethyl-propyl)amino]-s-triazin-2-yl]-3-azabicyclo[3 · 2 · 2]nonane | 0.05 |
| Triglycerol Pentaoleate | 10.0 |
| Benzyl Alcohol | 2.0 |
| Sesame Oil | 5.0 |
| Soy Lecithin 95% P.C. | 0.8 |
| Glycerine U.S.P. | 2.25 |
| Water for Injection | qs |

A 25.0 mg amount of 3-[4,6-bis[(1,1-2,2-tetramethylpropyl)amino]-s-triazin-2-yl]-3-azabicyclo[3.2.2]nonane was dissolved by stirring in a mixture of 5.0 g of triglycerol pentaoleate, 1.0 g of benzyl alcohol, 2.5 g of sesame oil, 0.4 g of soy lecithin and 1.125 g of glycerine at room temperature. The mixture was diluted to exactly 50.0 ml with water for injection, then mixed and sonicated for 20 seconds using a Branson Sonifier driver at a direct current setting of 6–7 amperes.

EXAMPLE 12

Preparation of an Oral Emulsion Drug Delivery System Containing 1 mg/ml of Antiarthritic Drug

| Ingredient | Amount % W/V |
|---|---|
| 3-[4,6-Bis[(1,1-2,2-tetramethyl-propyl)amino]-s-triazin-2-yl]-3-azabicyclo[3 · 2 · 2]nonane | 0.1 |
| Triglycerol Pentaoleate | 10.0 |
| Benzyl Alcohol | 2.0 |
| Sesame Oil | 5.0 |
| Soy Lecithin 95% P.C. | 0.8 |
| Glycerine U.S.P. | 2.25 |
| Water for Injection | qs |

A 50.0 mg amount of 3-[4,6-bis[(1,1-2,2-tetramethylpropyl)amino]-s-triazin-2-yl]-3-azabicyclo[3.2.2]nonane was dissolved by stirring in a mixture of 5.0 g of triglycerol pentaoleate, 1.0 g of benzyl alcohol, 2.5 g of sesame oil, 0.4 g of soy lecithin and 1.125 g of glycerine at room temperature. The mixture was diluted to exactly 50.0 ml with water for injection, then mixed and sonicated for 20 seconds using a Branson Sonifier driver at a direct current setting of 6–7 amperes.

EXAMPLE 13

Preparation of an Oral Emulsion Drug Delivery System Containing 4 mg/ml of Antiarthritic Drug

| Ingredient | Amount % W/V |
|---|---|
| 3-[4,6-Bis[(1,1-2,2-tetramethyl-propyl)amino]-s-triazin-2-yl]-3-azabicyclo[3 · 2 · 2]nonane | 0.4 |
| Triglycerol Pentaoleate | 10.0 |
| Benzyl Alcohol | 2.0 |
| Sesame Oil | 5.0 |
| Soy Lecithin 95% P.C. | 0.8 |
| Glycerin U.S.P. | 2.25 |
| Water for Injection | qs |

A 100.0 mg amount of 3-[4,6-bis[(1,1-2,2-tetramethylpropyl)amino]-s-triazin-2-yl]-3-azabicyclo[3.2.2]nonane was dissolved by swirling in a mixture of 2.5 g of triglycerol pentaoleate, 500 mg of benzyl alcohol, 1.25 g of sesame oil, 200 mg of soy lecithin and 563 mg of glycerine at room temperature. The mixture was diluted to exactly 25.0 ml with water for injection, then mixed and sonicated as for Example 11.

EXAMPLE 14

Preparation of an Oral Emulsion Drug Delivery System Containing 8 mg/ml of Antiarthritic Drug

| Ingredient | Amount % W/V |
|---|---|
| 3-[4,6-Bis[(1,1-2,2-tetramethyl-propyl)amino]-s-triazin-2-yl]-3-azabicyclo[3 · 2 · 2]nonane | 0.8 |
| Triglycerol Pentaoleate | 20.0 |
| Benzyl Alcohol | 4.0 |
| Sesame Oil | 10.0 |
| Soy Lecithin 95% P.C. | 1.6 |
| Glycerine U.S.P. | 2.25 |
| Water for Injection | qs |

A 400 mg amount of 3-[4,6-bis[(1,1-2,2-tetramethylpropyl)amino]-s-triazin-2-yl]-3-azabicyclo[3.2.2]nonane was dissolved by stirring in a mixture of 10.0 g of triglycerol pentaoleate, 2.0 g of benzyl alcohol, 5.0 g of sesame oil, 800 mg of soy lecithin and 2.25 g of glycerine at room temperature. The mixture was diluted to exactly 50.0 ml with water for injection, then mixed and sonicated as for Example 11.

EXAMPLE 15

Preparation of an Oral Emulsion Drug Delivery System Containing 8 mg/ml of Antiarthritic Drug and dl-α-Tocopherol as Antioxidant

| Ingredient | Amount % W/V |
|---|---|
| 3-[4,6-Bis[(1,1-2,2-tetramethyl-propyl)amino]-s-triazin-2-yl]-3-azabicyclo[3·2·2]nonane | 0.8 |
| Triglycerol Pentaoleate | 20.0 |
| Benzyl Alcohol | 4.0 |
| Sesame Oil | 10.0 |
| Soy Lecithin 95% P.C. | 1.6 |
| dl-α-Tocopherol | 0.1 |
| Glycerine | 4.5 |
| Water for Injection | qs |

A 400 mg amount of 3-[4,6-bis[(1,1-2,2-tetramethylpropyl)amino]-s-triazin-2-yl]-3-azabicyclo[3.2.2]nonane was dissolved by stirring in a mixture of 10.0 g of triglycerol pentaoleate, 2.0 g of benzyl alcohol, 5.0 g of sesame oil, 800 mg of soy lecithin, 50.0 mg of dl-α-tocopherol and 2.25 g of glycerine at room temperature. The mixture was diluted to exactly 50.0 ml with water for injection, then mixed and sonicated as for Example 11.

A comparison of representative formulae of the new emulsion drug delivery systems of the present invention for bisantrene base with known commercial intravenous fat emulsion products is shown in Table III. It is anticipated that the new emulsion systems described in Table III will find application with other known water insoluble hydrophobic ionizable drugs such as Adriamycin, Amphotericin B, Indomethacin, Terfenadine, Promethazine, chlorpromazine, Hydroxyzine and the like as hereinabove described in Table IA.

TABLE III

Comparison of Known Intravenous Fat Emulsions and New Emulsion Drug Delivery Systems for Bisantrene

| Component % W/V | Intralipid ® | Liposyn ® | Lipomul ® | Emulsions | | | | | | | | |
|---|---|---|---|---|---|---|---|---|---|---|---|---|
| | | | | 1 (Ex. 1) | 2 (Ex. 2) | 3 (Ex. 3) | 4 (Ex. 4) | 5 (Ex. 5) | 6 (Ex. 6) | 7 (Ex. 7) | 8 (Ex. 8) | 9 (Ex. 9) |
| Soybean Oil | 10 | | | | | | | | | 5.0 or 7.0 | 7.0 | 7.0 |
| Safflower Oil | | 10 | | | | | | | | | | |
| Cottonseed Oil | | | 15 | | | | | | | | | |
| Super Refined Sesame Oil | | | | 3 | 5 | 5 | 5 | 5 | 5 | | | |
| Sorbitan Triisosterate | | | | | 10 | | | | | | | |
| Triglycerol Diisostearate | | | | | | 10 | | | | | | |
| Triglycerol Pentaoleate 3G 4.50 | | | | | | | 10 | 10 | 10 | 10 | | |
| Soybean Phosphatides Soy Lecithin | | | 2.5 | | | | 0.8 | 0.8 | 0.8 | | 1.2 | 1.0 | 1.0 |
| Egg Phosphatide | 1.2 | 1.2 | | | | | | | | 0.8 | | |
| Egg Lecithins | | | | | | | | | | | | |
| Pluronic F-68 | | | 0.3 | 0.75 | 0.5 | | | | | | | |
| Glycerol (Glycerine) | 2.25 | 2.5 | | | | | 2.25 | 2.25 | 2.25 | 2.25 | 2.25 | 2.25 | 2.25 |
| Benzyl Alcohol | | | | 2 | 3 | 2 | 2 | 2 | 2 | 0.9 | 0.9 | 0.9 |
| dl-α-Tocopherol | | | | | | | | 0.002 | 0.002 | 0.01 | 0.01 | 0.01 |
| Dextrose | | | 4 | | | | | | | | | |
| Oleic Acid | | | | | | | | 0.75 | 0.75 | 0.7 | 0.4 | 0.4 |
| Hexanoic Acid | | | | | | | | | | 0.1 | 0.1 | 0.1 |
| Linolenic | | | | | | | | | | | 0.3 | 0.3 |
| Polyvinylpyrrolidone Type NP-K90 | | | | | | | | | | | | 0.04 |
| Bisantrene Base | | | | 0.05 | 0.05 | 0.05 | 0.1 | 0.1 | 0.1 | 0.2 | 0.2 | 0.2 |
| Water for | 100 | 100 | 100 | Q.S. | Q.S. | Q.S. | Q.S. | Q.S. | Q.S. | Q.S. | Q.S. | Q.S. |

TABLE III-continued

Comparison of Known Intravenous Fat Emulsions and New Emulsion Drug Delivery Systems for Bisantrene

| Component % W/V | Intra- lipid ® | Lipo- syn ® | Lipo- mul ® | Emulsions | | | | | | | | |
|---|---|---|---|---|---|---|---|---|---|---|---|---|
| | | | | 1 (Ex. 1) | 2 (Ex. 2) | 3 (Ex. 3) | 4 (Ex. 4) | 5 (Ex. 5) | 6 (Ex. 6) | 7 (Ex. 7) | 8 (Ex. 8) | 9 (Ex. 9) |
| Injection | | | | 100 | 100 | 100 | 100 | 100 | 100 | 100 | 100 | 100 |

The emulsion drug delivery system formulation of Emulsions 3 and 4 in Table III was tested in two species of animals, for peripheral vein irritation in order to determine the occurrence of local injection site adverse reactions. Also tested was a 1.0 mg/ml solution of bisantrene hydrochloride in 5% dextrose/water and a composition of the Emulsion 3 vehicle (Example 10) without bisantrene base. The two species of animals used were rabbits and dogs. The formulations were given intravenously in a peripheral vein using a Butterfly infusion set (Becton, Dickenson Co., Inc., Rutherford, N.J.). The marginal ear vein was used in the rabbit and the saphenous or the cephalic vein of the leg was used in the dog.

The formulations were given by slow intravenous infusion using a Sage syringe pump (Sage Instruments, Orion Research Inc., Cambridge, MA) over a 2 hour period. The animals were restrained but unanesthetized during the infusion. After the infusion, the animals were returned to their cages and offered food. The animals were sacrificed one day after the infusion.

At sacrifice, the infused vein was opened from the point of infusion and cardiad for several centimeters. The condition of the vein, its intima and the surrounding parenchyma, as well as the presence or absence of orange-yellow material and/or clots in the vein, were recorded in Tables IV and V.

The results in Tables IV and V show that when bisantrene base was contained in an emulsion drug delivery system as described in Example 3 (Emulsion #3) and Example 4 (Emulsion #4) and was infused into the marginal ear vein of rabbits and the peripheral vein of dogs the presence of yellow or yellow-orange deposits on the vascular lumen was greatly reduced when compared to results obtained when bisantrene hydrochloride in 5% dextrose/water for injection was infused in the same manner.

TABLE IV

Comparative Toxicity Data of the Intravenous Infusion of an Emulsion Formulation with Bisantrene Base, Emulsion Vehicle Without Bisantrene Base and Bisantrene Hydrochloride in 5% Dextrose/Water in the Marginal Ear Vein of Rabbits
Gross Postmortem Findings

| Vehicle | Sex | External | | | Subcutaneous | | | Vascular Lumen | |
|---|---|---|---|---|---|---|---|---|---|
| | | Reddened | Swollen | Yellow Deposit | Hemorrhage | Edema | Yellow Deposit | Blood Clot | Yellow Deposit |
| Bisantrene HCl in 5% Dextrose/Water | F | + | ++ | + | − | ++ | ++ | ++ | + |
| | M | − | − | − | − | + | − | − | + |
| Emulsion #4 Vehicle Without Bisantrene Base (Ex. 10) | F | − | − | − | − | + | − | + | − |
| | M | − | − | − | − | − | − | − | − |
| Emulsion #4 with Bisantrene Base (Ex. 4) | F | ++ | + | − | ++ | ++ | − | − | − |
| | M | ++ | + | − | − | ++ | + | +++ | + |

+ = Positive or present.
− = Negative or absent.

TABLE V

Comparative Acute and Local Toxicity Data of the Intravenous Infusion of an Emulsion Formulation with Bisantrene Base, Emulsion Vehicle Without Bisantrene Base and Bisantrene Hydrochloride in 5% Dextrose/Water in the Peripheral Vein of Dogs
Gross Postmortem Findings

| Vehicle | External | | | Vascular-Lumen | | |
|---|---|---|---|---|---|---|
| | Red or Grey Discoloration | Swelling | Yellowish Discoloration | Blood Clot | Yellow-Orange Deposit | Yellow Color of Intima |
| Bisantrene HCl in 5% Dextrose/Water | − | − | − | ++ | +++ | − |
| | + | ++ | − | +++ | +++ | + |
| Emulsion #3 Vehicle Without Bisantrene Base (Ex. 10) | − | − | − | + | − | − |
| | − | − | − | ++ | − | − |
| Emulsion #3 with Bisantrene Base (Ex. 3) | − | − | − | + | − | + |
| | + | + | − | ++ | − | + |

What is claimed is:

1. A composition of matter for delivery by hydrophobic drugs comprising:
 (a) a hydrophobic drug;
 (b) an oleaginous vehicle or oil phase said oleaginous vehicle or oil phase being substantially free of BHT or BHA;
 (c) a co-surfactant or emulsifier;
 (d) a co-surfactant or auxiliary emulsifier; and
 (e) benzyl alcohol as a co-solvent;
wherein the hydrophobic drug may be a sparingly water liquid and may be a basic drug which has an ionization constant lower or nearer the physiological pH or an acid drug which has an ionization constant higher or nearer the physiological pH.

2. The composition of matter as recited in claim 1 comprising:

| Ingredient | Percent Range W/V |
|---|---|
| Hydrophobic drug | .001–1.0 |
| Triglycerol Pentaoleate | 5.0–20.0 |
| Benzyl Alcohol | 0.2–4.0 |
| Sesame Oil | 1.6–10.0 |
| Soy or Egg Lecithin | 0.4–1.6 |
| dl-α-Tocopherol | 0.0–0.1 |
| Glycerine U.S.P. | 2.0–4.5 |
| Water for injection qs ad | 100. |

3. The composition of matter as recited in claim 1 comprising:

| Ingredient | Percent Range W/V |
|---|---|
| Hydrophobic drug | 0.001–1.0 |
| Triglycerol Pentaoleate | 0.0–10.0 |
| Benzyl Alcohol | 0.2–4.0 |
| Sesame Oil | 0.0–5.0 |
| Soy or Egg Lecithin | 0.4–1.6 |
| Oleic Acid | 0.4–1.2 |
| Hexanoic Acid | 0.0–1.0 |
| Linolenic Acid | 0.0–1.0 |
| Soybean Oil | 3.0–10.0 |
| dl-α-Tocopherol | 0.002–0.1 |
| Polyvinylpyrrolidone | 0.0–0.2 |
| Glycerine U.S.P. | 2.0–4.0 |
| Water for injection qs ad | 100. |

4. The composition of matter as recited in claim 1 comprising: Percent

| Ingredient | Range W/V |
|---|---|
| Hydrophobic drug | .001–1.0 |
| Sorbitan Triisostearate or Triglycerol Diisostearate | 10.0–20.0 |
| Benzyl Alcohol | 2.0–3.0 |
| Sesame Oil | 3.0–5.0 |
| [Pluronic ® F-68] Polyethylene polypropylene glycol | 0.5–0.75 |
| Water for injection qs ad | 100. |

5. The composition of matter as recited in claim 1 comprising:

| Ingredient | Percent W/V |
|---|---|
| Hydrophobic drug | 0.05–0.8 |
| Triglycerol Pentaoleate | 10.0–20.0 |
| Benzyl Alcohol | 2.0–4.0 |
| Sesame Oil | 5.0–10.0 |
| Soy or Egg Lecithin | 0.8–1.6 |
| Glycerine U.S.P. | 2.25 |
| Water for injection qs ad | 100. |

6. The composition of matter as recited in claim 1 comprising:

| Ingredient | Percent W/V |
|---|---|
| Hydrophobic drug | 0.8 |
| Triglycerol Pentaoleate | 20.0 |
| Benzyl Alcohol | 4.0 |
| Sesame Oil | 10.0 |
| Soy Lecithin | 1.6 |
| dl-α-Tocopherol | 0.1 |
| Glycerine U.S.P. | 4.5 |
| Water for injection qs ad | 100. |

7. The composition of matter as recited in claim 1 comprising:

| Ingredient | Percent W/V |
|---|---|
| Hydrophobic drug | 0.1 |
| Triglycerol Pentaoleate | 10.0 |
| Benzyl Alcohol | 2.0 |
| Sesame Oil | 5.0 |
| Soy or Egg Lecithin | 0.8 |
| Oleic Acid | 0.75 |
| dl-α-Tocopherol | 0.002 |
| Glycerine U.S.P. | 2.25 |
| Water for injection qs ad | 100. |

8. The composition of matter as recited in claim 1 comprising:

| Ingredient | Percent W/V |
|---|---|
| Hydrophobic drug | 0.2 |
| Soybean Oil | 5.0–7.0 |
| Benzyl Alcohol | 0.9 |
| Soy Lecithin | 1.0–1.2 |
| Oleic Acid | 0.4–0.7 |
| Hexanoic Acid | 0.1 |
| Linolenic Acid | 0.0–0.3 |
| dl-α-Tocopherol | 0.01 |
| Glycerine U.S.P. | 2.25 |
| Polyvinylpyrrolidone | 0.0–0.04 |
| Water for injection qs ad | 100. |

9. The composition of matter as recited in claim 1 comprising:

| Ingredient | Percent Range W/V |
|---|---|
| Hydrophobic drug | 0.05 |
| Sorbitan Triisostearate or Triglycerol Diisostearate | 10.0 |
| Benzyl Alcohol | 2.0–3.0 |
| Sesame Oil | 3.0–5.0 |
| [Pluronic ® F-68] Polyethylene polypropylene glycol | 0.5–0.75 |
| Water for injection qs ad | 100. |

10. The composition of matter as recited in claim 5, in which the hydrophobic drug is bis(2-imidazolin-2-ylhydrazone)-9,10-anthracenedicarboxaldehyde.

11. A composition in accordance with claim 4, in which the hydrophobic drug is 3-[4,6-bis[(1,1-2,2-tetramethylpropyl)amino]-s-triazin-2-yl]-3-azabicyclo[3.2.2]nonane.

12. The composition of matter as recited in claim 6, in which the hydrophobic drug is 3-[4,6-bis[(1,1-2,2-tetramethylpropyl)amino]-s-triazin-2-yl]-3-azabicyclo[3.2.2]nonane.

13. The composition of matter as recited in claim 7, in which the hydrophobic drug is bis(2-imidazolin-2-ylhydrazone)-9,10-anthracenedicarboxaldehyde.

14. The composition of matter as recited in claim 8, in which the hydrophobic drug is bis(2-imidazolin-2-ylhydrazone)-9,10-anthracenedicarboxaldehyde.

15. The composition of matter as recited in claim 9, in which the hydrophobic drug is bis(2-imidazolin-2-ylhydrazone)-9,10-anthracenedicarboxaldehyde.

16. The composition of matter as recited in claim 1, which consists essentially of:

| Ingredient | Percent Range W/V |
|---|---|
| Hydrophobic Drug | .001–1.0 |
| Sorbitan Triisostearate or Triglycerol Diisostearate | 10.0–20.0 |
| Benzyl Alcohol | 2.0–3.0 |
| Sesame Oil | 3.0–5.0 |
| Poloxamer | 0.5–0.75 |
| Water for injection qs ad | 100. |

17. The composition of matter as recited in claim 1, which consists essentially of:

| Ingredient | Percent W/V |
|---|---|
| Hydrophobic Drug | 0.05–0.8 |
| Triglycerol Pentaoleate | 10.0–20.0 |
| Benzyl Alcohol | 2.0–4.0 |
| Sesame Oil | 5.0–10.0 |
| Soy or Egg Lecithin | 0.8–1.6 |
| Glycerine U.S.P. | 2.25 |
| Water for injection qs ad | 100. |

18. The composition of matter as recited in claim 1, which consists essentially of:

| Ingredient | Percent W/V |
|---|---|
| Hydrophobic Drug | 0.8 |
| Triglycerol Pentaoleate | 20.0 |
| Benzyl Alcohol | 4.0 |
| Sesame Oil | 10.0 |
| Soy Lecithin | 1.6 |
| dl-α-Tocopherol | 0.1 |
| Glycerine U.S.P. | 4.5 |
| Water for injection qs ad | 100. |

19. The composition of matter as recited in claim 1, which consists essentially of:

| Ingredients | Percent W/V |
|---|---|
| Hydrophobic Drug | 0.1 |
| Triglycerol Pentaoleate | 10.0 |
| Benzyl Alcohol | 2.0 |
| Sesame Oil | 5.0 |
| Soy or Egg Lecithin | 0.8 |
| Oleic Acid | 0.75 |
| dl-α-Tocopherol | 0.002 |
| Glycerine U.S.P. | 2.25 |
| Water for injection qs ad | 100. |

20. The composition of matter as recited in claim 1, which consits essentially of:

| Ingredient | Percent W/V |
|---|---|
| Hydrophobic drug | 0.2 |
| Soybean Oil | 5.0–7.0 |
| Benzyl Alcohol | 0.9 |
| Soy Lecithin | 1.0–1.2 |
| Oleic Acid | 0.4–0.7 |
| Hexanoic Acid | 0.1 |
| Linolenic Acid | 0.0–0.3 |
| dl-α-Tocopherol | 0.01 |
| Glycerine U.S.P. | 2.25 |
| Polyvinylpyrrolidone | 0.0–0.04' |
| Water for injection qs ad | 100. |

21. The composition of matter as recited in claim 1, which consists essentially of:

| Ingredient | Percent W/V |
|---|---|
| Hydrophobic drug | 0.05 |
| Sorbitan Triisostearate or Triglycerol Diisostearate | 10.0 |
| Benzyl Alcohol | 2.0–3.0 |
| Sesame Oil | 3.0–5.0 |
| Poloxamer | 0.5–0.75 |
| Water for injection qs ad | 100. |

22. The composition of matter as recited in claim 16, in which the hydrophobic drug is bis(2-imidazolin-2-ylhydrazone)-9,10-anthracenedicarboxaldehyde.

23. A composition in accordance with claim 17, in which the hydrophobic drug is bis(2-imidazolin-2-ylhydrazone)-9,10-anthracenedicarboxaldehyde.

24. The composition of matter as recited in claim 18, in which the hydrophobic drug is bis(2-imidazolin-2-ylhydrazone)-9,10-anthracenedicarboxaldehyde.

25. The composition of matter as recited in claim 19, in which the hydrophobic drug is bis(2-imidazolin-2-ylhydrazone)-9,10-anthracenedicarboxaldehyde.

26. The composition of matter as recited in claim 20, in which the hydrophobic drug is bis(2-imidazolin-2-ylhydrazone)-9,10-anthracenedicarboxaldehyde.

27. The composition of matter as recited in claim 21, in which the hydrophobic drug is bis(2-imidazolin-2-ylhydrazone)-9,10-anthracenedicarboxaldehyde.

* * * * *